United States Patent
Kee et al.

(10) Patent No.: US 9,393,210 B2
(45) Date of Patent: *Jul. 19, 2016

(54) CAPSULES CONTAINING HIGH DOSES OF LEVODOPA FOR PULMONARY USE

(71) Applicant: Civitas Therapeutics, Inc., Chelsea, MA (US)

(72) Inventors: Kevin D. Kee, Somerville, MA (US); Ernest D. Penachio, Haverhill, MA (US); Abhijit Kamerkar, Boston, MA (US); Michael M. Lipp, Framingham, MA (US); Richard P. Batycky, Newton, MA (US)

(73) Assignee: Civitas Therapeutics, Inc., Chelsea, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/575,454

(22) Filed: Dec. 18, 2014

(65) Prior Publication Data

US 2015/0320711 A1  Nov. 12, 2015

Related U.S. Application Data (63) Continuation of application No. 14/174,179, filed on Feb. 6, 2014, now Pat. No. 8,945,612, which is a continuation of application No. 13/945,160, filed on Jul. 18, 2013, now Pat. No. 8,685,442, which is a continuation of application No. 13/679,245, filed on Nov. 16, 2012, now Pat. No. 8,545,878.

(60) Provisional application No. 61/724,781, filed on Nov. 9, 2012.

(51) Int. Cl.
| | |
|---|---|
| *A61K 9/00* | (2006.01) |
| *A61K 9/48* | (2006.01) |
| *A61K 9/16* | (2006.01) |
| *A61K 31/198* | (2006.01) |

(52) U.S. Cl.
CPC ............. *A61K 9/4858* (2013.01); *A61K 9/0073* (2013.01); *A61K 9/0075* (2013.01); *A61K 9/1611* (2013.01); *A61K 9/1617* (2013.01); *A61K 9/485* (2013.01); *A61K 9/4808* (2013.01); *A61K 9/4816* (2013.01); *A61K 31/198* (2013.01)

(58) Field of Classification Search
None
See application file for complete search history.

(56) References Cited

U.S. PATENT DOCUMENTS

| | | | | |
|---|---|---|---|---|
| 5,756,123 A * | 5/1998 | Yamamoto | ........... | A61K 9/4816 424/451 |
| 6,514,482 B1 * | 2/2003 | Bartus | ........... | A61K 9/008 128/203.15 |
| 6,531,153 B2 * | 3/2003 | Seth | ........... | A61K 9/2013 424/486 |
| 6,613,308 B2 * | 9/2003 | Bartus | ........... | A61K 9/0075 128/203.15 |
| 6,932,984 B1 * | 8/2005 | Babtsov | ........... | A61K 9/1694 264/4.33 |
| RE43,711 E * | 10/2012 | Jackson | ........... | A61K 9/0075 424/46 |
| 8,821,928 B2 * | 9/2014 | Hemmingsen | ........... | A61K 9/2072 424/457 |
| 2003/0180352 A1 * | 9/2003 | Patel | ........... | A61K 9/1617 424/465 |
| 2004/0028735 A1 * | 2/2004 | Kositprapa | ........... | A61K 9/2013 424/468 |
| 2004/0265242 A1 * | 12/2004 | Bartus | ........... | A61K 9/0075 424/46 |
| 2006/0216345 A1 * | 9/2006 | Dhavse | ........... | A61K 9/1694 424/451 |
| 2006/0222699 A1 * | 10/2006 | Gilinski | ........... | A61K 9/4816 424/451 |
| 2007/0275060 A1 * | 11/2007 | Befumo | ........... | A61K 9/2009 424/468 |
| 2008/0066741 A1 * | 3/2008 | LeMahieu | ........... | A61M 11/041 128/200.21 |
| 2010/0074947 A1 * | 3/2010 | Brown | ........... | A61K 9/4816 424/452 |
| 2010/0316712 A1 * | 12/2010 | Nangia | ........... | A61K 9/0065 424/472 |
| 2010/0330170 A1 * | 12/2010 | Gilinski | ........... | A61K 9/4816 424/452 |
| 2011/0151008 A1 * | 6/2011 | Jackson | ........... | A61K 9/0075 424/489 |
| 2011/0268666 A1 * | 11/2011 | Friedman | ........... | A61K 9/0065 424/44 |
| 2012/0164233 A1 * | 6/2012 | Bhargava | ........... | A61K 9/4808 424/494 |
| 2014/0088202 A1 * | 3/2014 | Cade | ........... | A61K 9/4816 514/780 |

* cited by examiner

*Primary Examiner* — Robert A Wax
*Assistant Examiner* — Olga V Tcherkasskaya
(74) *Attorney, Agent, or Firm* — Elmore Patent Law Group, P.C.; Darlene A. Vanstone; Carolyn S. Elmore (57) ABSTRACT

The present invention provides a capsule containing an inhalable powder composition wherein the composition comprises about 75% by weight or more levodopa, dipalmitoylphosphatidylcholine (DPPC) and a salt characterized by a working density of less than about 100 g/L. The invention further provides a capsule containing an inhalable powder composition wherein the composition comprises about 75% by weight or more levodopa, dipalmitoylphosphatidylcholine (DPPC) and a salt characterized by a working density of less than about 100 g/L wherein the capsule material comprises hydroxypropylmethylcellulose (HPMC) and titanium dioxide.

15 Claims, 4 Drawing Sheets

CAPSULES CONTAINING HIGH DOSES OF LEVODOPA FOR PULMONARY USE

RELATED APPLICATION

This application is a continuation of U.S. application Ser. No. 14/174,179, filed Feb. 6, 2014 which is a continuation of U.S. application Ser. No. 13/945,160, filed Jul. 18, 2013, now U.S. Pat. No. 8,685,442, which is a continuation of U.S. application Ser. No. 13/679,245, filed Nov. 16, 2012, now U.S. Pat. No. 8,545,878 which claims the benefit of U.S. Provisional Application No. 61/724,781, filed on Nov. 9, 2012. The entire teachings of the above applications are incorporated herein by reference.

BACKGROUND OF THE INVENTION

Parkinson's disease is a debilitating disease caused by the death of dopamine neurons in the central nervous system. Parkinson's disease patients experience life altering symptoms of tremors, slowness in moving, and difficulty walking. While no drugs exist which cure the disease or stop its progression, a number of drugs exist to help with symptoms. The most commonly used drug and the drug all Parkinson's patients eventually use is levodopa. Levodopa (also referred to herein as "levodopa") is currently supplied in tablets with or without one or two other drugs. The other drugs typically function to prevent the body from metabolizing the levodopa before it can take its effect. Many patients initially respond well to levodopa treatment, but over time the effect becomes diminished. Patients typically start increasing their levodopa dosage as their disease progresses. A patient at the early stages of taking levodopa may only take 200 mg of levodopa per day, but a later stage patient could be taking 600 to 1200 mg of levodopa a day. Once the doses increase, patients become prone to dyskinesias. Dyskinesias are involuntary movements due to too much levodopa. When patient levodopa concentrations go to low, patients experience freezing episodes where the patient has significant difficulty moving. Once a freezing episode occurs, patient can take a tablet of levodopa, but they have to wait until the levodopa is absorbed to become unfrozen. Further complicating the freezing problem is that Parkinson's patients have poor stomach motility resulting in slow drug absorption. An inhalable formulation of levodopa could help patients with these freezing issues. A difficulty in creating an inhalable levodopa product is delivering enough dose to the patient, since levodopa is a high dose drug. Another difficulty is delivering an inhaled drug to a Parkinsons' patient. Since these patients are movement impaired, they need a quick and simple process to inhale the levodopa.

In addition to the above difficulties with delivering levodopa, a number of difficulties exist with delivering high doses of any drug by the pulmonary route. A dry powder containing a drug can vary greatly in density. Modifying the density of the powder can affect stability and the ability of the drug to reach the lungs appropriately. However, optimizing the density of the levodopa inhalable powder enables the effective delivery of high doses of levodopa to the patient by inhalation. Even if appropriate density can be reached for a high dose drug such as levodopa, the efficient emptying of the powder from the capsule is also a critical factor. If the emptying characteristics of the capsule are poor, the increased dosage achieved by optimal loading of the powder into the capsule is diminished.

A number of important challenges exist to deliver a high dose of levodopa to a Parkinson's patient while also keeping the drug product stable and easy to use for the patient. Pulmonary powders may be provided in amorphous form as amorphous forms of a compound have faster dissolution and would be more likely to show a fast onset of action. Despite the advantage of fast onset of action for an amorphous powder, amorphous powders are difficult to manufacture and difficult to keep stable under long term storage conditions, as required by the drug regulatory agencies. Further, filling large volumes of amorphous powders in a capsule can be challenging due to electrostatic charges. For crystalline powders, increasing the relative humidity can reduce the electrostatic charge of the powder and allow for better capsule filling, but increasing the relative humidity is not a viable option for an amorphous powder. Amorphous powders become prone to amorphous to crystalline transitions under elevated relative humidity. Thus, a significant difficulty exists in identifying a fast acting amorphous powder which is stable with a low electrostatic charge.

SUMMARY OF THE INVENTION

The present invention provides a capsule containing an inhalable powder composition wherein the composition comprises about 75% by weight or more levodopa, dipalmitoylphosphatidylcholine (DPPC) and a salt characterized by a working density of less than about $0.1$ $g/cm^3$. The invention further provides a capsule containing an inhalable powder composition wherein the composition comprises about 75% by weight or more levodopa, dipalmitoylphosphatidylcholine (DPPC) and a salt characterized by a working density of less than about $0.1$ $g/cm^3$ wherein the capsule material comprises hydroxypropylmethylcellulose (HPMC) and titanium dioxide.

DETAILED DESCRIPTION OF THE INVENTION

The capsules according to the invention are for use in an inhalation device and contain, as the inhalable powder, levodopa mixed with one or more physiologically acceptable excipients, characterized in that the powder has a working density (also referred to herein as "bulk density") of about 100 g/L or less which can also be expressed as about 0.1 g/cm$^3$ or less. Because levodopa is a high dose drug and delivering large amounts of levodopa is difficult for pulmonary delivery, it would be desirable to have a low density powder. A low density powder could allow for a significantly higher dose of levodopa per capsule than an average density powder. A difficulty is that low density levodopa powders are difficult to achieve while still allowing for a powder that can be easily filled into a capsule. In one embodiment the invention provides capsules containing an inhalable powder comprising levodopa wherein the capsule has superior emptying characteristics upon delivery of the powder from the capsule upon actuation when used in conjunction with an inhaler. Superior emptying from the capsule is an important characteristic of a capsule containing an inhalable powder comprising levodopa.

The capsules for inhalation according to the invention are filled with inhalable powder containing levodopa, wherein that the powder has a working density of less than about 0.1 g/cm$^3$ and preferably has a working density of between about 0.02 g/cm$^3$ and 0.08 g/cm$^3$.

The term "working density" as used herein is interchangeable with the term "bulk density" and is defined herein as the weight of the powder (m) divided by the volume it occupies (Vo) and is expressed herein as grams per liter (g/L) as determined by measurement in a graduated cylinder. Briefly, a graduated cylinder is first weighed, filled with powder without compacting, leveled if necessary without compacting and weighed again. The unsettled apparent volume is read to the nearest graduated unit. The working density is calculated by the formula m/Vo. Working density may also be expressed for example in grams per cubic centimeter (g/cm$^3$). In one embodiment the working density is less than 0.1 g/cm$^3$. In one embodiment the working density ranges from about 0.02 g/cm$^3$ to about 0.05 g/cm$^3$.

In one embodiment, the capsules contain powder with a working density between about 0.03 g/cm$^3$ to about 0.06 g/cm$^3$. In another embodiment, the capsules contain powder with a working density between about 0.04 g/cm$^3$ to about 0.05 g/cm$^3$. In a further embodiment, the capsules contain powder with a working density of about 0.04 g/cm$^3$. In a further embodiment, the capsules contain powder with a working density of about 0.045 g/cm$^3$. In a further embodiment, the capsules contain powder with a working density of about 0.05 g/cm$^3$. In a further embodiment, the capsules contain powder with a working density of about 0.035 g/cm$^3$. In a further embodiment, the capsules contain powder with a working density of about 0.03 g/cm$^3$. In one embodiment, the capsules contain powder with a working density between about 0.03 g/cm$^3$ to about 0.05 g/cm$^3$. In another embodiment, the capsules contain powder with a working density between about 0.04 g/cm$^3$ to about 0.06 g/cm$^3$. In another embodiment, the capsules contain powder with a working density between about 0.05 g/cm$^3$ to about 0.06 g/cm$^3$. In another embodiment, the capsules contain powder with a working density between about 0.06 g/cm$^3$ to about 0.07 g/cm$^3$.

The inhalable powder contained in the capsules of the invention comprises at least 50% by weight levodopa by weight of solids in the powder. In some embodiments, the inhalable powder in a capsule of this invention may contain at least 60%, 70%, 80%, 90% by dry weight or more levodopa. In one embodiment the inhalable powder contains about 75% by dry weight or more levodopa. In one embodiment, the inhalable powder contains about 85% by dry weight by weight or more levodopa. In one embodiment the inhalable powder in the capsule contains about 90% by dry weight by weight or more levodopa. In one embodiment, the inhalable powder in the capsule contains between 80-95% by dry weight levodopa of solids in the powder. In one embodiment, the inhalable powder in the capsule contains between 85-95% by dry weight levodopa of solids in the powder. In one embodiment, the inhalable powder in the capsule contains between 88-92% by dry weight levodopa of solids in the powder.

The inhalation powder may contain additional excipients. Examples of excipients include salts such as sodium chloride (NaCl), sodium citrate, sodium lactate, and potassium chloride and phospholipids such as dipalmitoylphosphatidylcholine (DPPC) dilauroylphosphatidylcholine (DLPC), disaturated-phosphatidylcholine (DSPC). In one embodiment, the capsule contains a powder comprising 90% levodopa, 8% dipalmitoylphosphatidylcholine, and 2% sodium chloride as measured by % of solids in the powder. In one embodiment the capsule contains an inhalable powder having a dry weight ratio of 90:8:2 of levodopa:DPPC:NaCl. In another embodiment the capsule contains an inhalable powder having a dry weight ratio of 90:5:5 of levodopa:DPPC:NaCl.

The capsules of the invention comprising the inhalable powders are useful for delivery of levodopa to the pulmonary system, in particular to the deep lung. The inhalable powder contained in the capsule of the invention is characterized by a fine particle fraction (FPF), geometric and aerodynamic dimensions and by other properties, as further described below.

Gravimetric analysis, using Cascade impactors, is a method of measuring the size distribution of airborne particles. The Andersen Cascade Impactor (ACI) is an eight-stage impactor that can separate aerosols into nine distinct fractions based on aerodynamic size. The size cutoffs of each stage are dependent upon the flow rate at which the ACI is operated. Preferably the ACI is calibrated at 60 L/min. In one embodiment, a two-stage collapsed ACI is used for particle optimization. The two-stage collapsed ACI consists of stages 0, 2 and F of the eight-stage ACI and allows for the collection of two separate powder fractions. At each stage an aerosol stream passes through the nozzles and impinges upon the surface. Particles in the aerosol stream with a large enough inertia will impact upon the plate. Smaller particles that do not have enough inertia to impact on the plate will remain in the aerosol stream and be carried to the next stage.

The ACI is calibrated so that the fraction of powder that is collected on a first stage is referred to herein as "fine particle fraction" or "FPF". The FPF corresponds to the percentage of particles that have an aerodynamic diameter of less than 5.6 μm. The fraction of powder that passed the first stage of the ACI and is deposited on the collection filter is referred to as "FPF(3.4)". This corresponds to the percentage of particles having an aerodynamic diameter of less than 3.4 μm.

The FPF fraction has been demonstrated to correlate to the fraction of the powder that is deposited in the lungs of the patient, while the FPF(3.4) has been demonstrated to correlate to the fraction of the powder that reaches the deep lung of a patient. In accordance with the invention, the FPF of the inhalable powder of the nominal dose contained in the capsule (i.e. the percentage of particles in the powder contained in the capsule that have an aerodynamic diameter of less than 5.6 μm) is about 40% or more. In one embodiment the FPF of the nominal dose of the inhalable powder contained in the capsule is about 50%, 60%, or 70%, or 80%, or 90%. In one embodiment the FPF is about 50% to about 60% of the nominal dose of the inhalable powder contained in the inhaler. In one embodiment the FPF is about 55% to about 65% of the nominal dose of the inhalable powder contained in the inhaler. In one embodiment the FPF is about 50% to about 70% of the nominal dose of the inhalable powder contained in the inhaler. In one embodiment the FPF is about 57% to about 62% of the nominal dose of the inhalable powder contained in the inhaler. In one embodiment the FPF is about 50% to about 69% of the nominal dose of the inhalable powder contained in the inhaler. In one embodiment the FPF is about 50%, 51%, 52%, 53%, 54%, 55%, 56%, 57%, 58%, 59%, 60%, 61%, 62%, 63%, 64%, or 65% of the nominal dose of the inhalable powder contained in the inhaler.

As used herein, the term "nominal powder dose" is the total amount of powder held in the capsule. As used herein, the term "nominal drug dose" is the total amount of Levodopa contained in the nominal amount of powder. The nominal powder dose is related to the nominal drug dose by the load percent of drug in the powder.

In one embodiment, the nominal powder dose is 25-50 mg by dry weight. In a further embodiment, the nominal powder dose is 25-40 mg by dry weight. In a still further embodiment, the nominal powder dose is 30-35 mg by dry weight or 32-38 mg by dry weight.

Another method for measuring the size distribution of airborne particles is the multi-stage liquid impinger (MSLI). The Multi-stage liquid Impinger (MSLI) operates on the same principles as the Anderson Cascade Impactor (ACI), but instead of eight stages there are five in the MSLI. Additionally, instead of each stage consisting of a solid plate, each MSLI stage consists of an methanol-wetted glass frit. The wetted stage is used to prevent bouncing and re-entrainment, which can occur using the ACI. The MSLI is used to provide an indication of the flow rate dependence of the powder. This can be accomplished by operating the MSLI at 30, 60, and 90 L/min and measuring the fraction of the powder collected on stage 1 and the collection filter. If the fractions on each stage remain relatively constant across the different flow rates then the powder is considered to be approaching flow rate independence.

In one embodiment, the inhalable powders of the invention have a tap density of less than about 0.4 g/cm$^3$. For example, the particles have a tap density less than about 0.3 g/cm$^3$, or a tap density less than about 0.2 g/cm$^3$, a tap density less than about 0.1 g/cm$^3$. Tap density can be measured by using instruments known to those skilled in the art such as the Dual Platform Microprocessor Controlled Tap Density Tester (Vankel, N.C.) or a GEOPYC™ instrument (Micrometrics Instrument Corp., Norcross, Ga., 30093). Tap density is a standard measure of the envelope mass density. Tap density can be determined using the method of USP Bulk Density and Tapped Density, United States Pharmacopia convention, Rockville, Md., 10$^{th}$ Supplement, 4950-4951, 1999. Features which can contribute to low tap density include irregular surface texture and porous structure. The envelope mass density of an isotropic particle is defined as the mass of the particle divided by the minimum sphere envelope volume within which it can be enclosed. In one embodiment of the invention, the particles have an envelope mass density of less than about 0.4 g/cm$^3$.

The inhalable powder of the invention has a preferred particle size, e.g., a volume median geometric diameter (VMGD) of at least about 1 micron (µm). The diameter of the spray-dried particles, for example, the VMGD, can be measured using a laser diffraction instrument (for example Helos manufactured by Sympatec, Princeton, N.J.). Other instruments for measuring particle diameter are well known in the art. The diameter of particles in a sample will range depending upon factors such as particle composition and methods of synthesis. The distribution of size of particles in a sample can be selected to permit optimal deposition to targeted sites within the respiratory tract.

The particles of the inhalable powder of the invention preferably have a "mass median aerodynamic diameter" (MMAD), also referred to herein as "aerodynamic diameter", between about 1 µm and about 5 µm or any subrange encompassed between about 1 µm and about 5 µm. For example, but not limited to, the MMAD is between about 1 µm and about 3 µm, or the MMAD is between about 3 µm and about 5 µm. Experimentally, aerodynamic diameter can be determined by employing a gravitational settling method, whereby the time for an ensemble of powder particles to settle a certain distance is used to infer directly the aerodynamic diameter of the particles. An indirect method for measuring the mass median aerodynamic diameter (MMAD) is the multi-stage liquid impinger (MSLI). The aerodynamic diameter, $d_{aer}$, can be calculated from the equation:

$$d_{aer} = d_g \sqrt{\rho_{tap}}$$

where $d_g$ is the geometric diameter, for example the MMGD, and $\rho$ is the powder density.

In one embodiment, the particles have a mass mean geometric diameter (MMGD) of between about 5 µm and about 18 µm. In another embodiment, the particles have a mass mean geometric diameter (MMGD) of between about 5 µm and about 12 µm. In another embodiment, the particles have a mass mean geometric diameter (MMGD) of between about 8 µm and about 10 µm. In another embodiment, the particles have a mass mean geometric diameter (MMGD) of between about 8 µm and about 15 µm.

Powders for use in capsules of this invention are typically produced by spray drying. In some cases, spray-drying can produce extremely dry particles which may have poor handling properties and may be difficult to compact into a capsule in a dense manner. A nitrogen source with a specified moisture level may be flown over, across, or through the dry powder to add a specific moisture content to the dry powder. Such moisture can provide the desired working density of the powder. Spray drying methods in accordance with the invention are described in the Examples herein and in U.S. Pat. Nos. 6,848,197 and 8,197,845, incorporated herein by reference.

The inhalable powder comprising levodopa as described above is used to fill capsules suitable for use in an inhaler. The term "capsule material" as used herein refers to the material from which the shell of the capsule for inhalation is made. In one embodiment, the capsule material according to the invention is selected from among gelatin, cellulose derivatives, starch, starch derivatives, chitosan and synthetic plastics.

If gelatin is used as the capsule material, examples according to the invention may be selected from among polyethyleneglycol (PEG), PEG 3350, glycerol, sorbitol, propyleneglycol, PEO-PPO block copolymers and other polyalcohols and polyethers. If cellulose derivatives are used as the capsule material, examples according to the invention may be selected from hydroxypropylmethylcellulose (HPMC), hydroxypropylcellulose, methylcellulose, hydroxymethylcellulose and hydroxyethylcellulose. If synthetic plastics are used as the capsule material, examples according to the invention may be selected from polyethylene, polycarbonate, polyester, polypropylene and polyethylene terephthalate. In one embodiment, the capsule material further comprises titanium dioxide. In one preferred embodiment the capsule comprises HPMC and titanium dioxide. In one embodiment, the capsule comprises carrageenan. In a further embodiment, the capsule comprises potassium chloride. In a still further embodiment, the capsule comprises, HPMC, carrageenan, potassium chloride, and titanium dioxide. In one embodiment, the capsule size is selected from 000, 00, 0, 1, or 2. In a specific embodiment, the capsule size is 00.

In one specific embodiment, the capsule is a hydroxypropylmethylcellulose (HPMC) capsule. In another specific embodiment, the capsule is a hydroxypropylmethylcellulose size 00 capsule. In one specific embodiment the capsule material comprises HPMC and titanium dioxide and the capsule size is 00.

In one embodiment, a 00 capsule contains between 15 and 50 grams of levodopa by dry weight. In another embodiment, a 00 capsule contains between 20 and 40 grams of levodopa by dry weight. In another embodiment, a 00 capsule contains between 25 and 35 grams of levodopa by dry weight. In another embodiment, a 00 capsule contains about 30, 31, 32, 33, 34, 35, 36, 37, 38, 39, or 40 grams of levodopa by dry weight.

In one aspect of the invention, the powders have low electrostatic charge to enable high dispersion from the capsule.

The capsules of the invention are particularly suitable for use in a dry powder inhaler for the delivery of a dry powder composition comprising levodopa to a patient afflicted with, for example, Parkinson's disease and in need of treatment with levodopa. The patient in need of treatment may require maintenance therapy for Parkinson's disease or rescue therapy for Parkinson's disease such as would be necessary in the case of an acute and/or freezing episode due to Parkinson's disease. In one embodiment, the capsules are used in a dry powder inhaler to deliver an effective amount of the dry powder composition to the patient in a single breath as is described in U.S. Pat. Nos. 6,858,199 and 7,556,798 incorporated herein by reference.

As used herein, the term "effective amount" means the amount needed to achieve the desired effect or efficacy. The actual effective amounts of drug can vary according to the specific drug or combination thereof being utilized, the particular composition formulated, the mode of administration, and the age, weight, condition of the patient, and severity of the episode being treated. In the case of a dopamine precursor, agonist or combination thereof it is an amount which reduces the Parkinson's symptoms which require therapy. Dosages for a particular patient are described herein and can be determined by one of ordinary skill in the art using conventional considerations, (e.g. by means of an appropriate, conventional pharmacological protocol). For example, effective amounts of oral levodopa range from about 50 milligrams (mg) to about 500 mg. In many instances, a common ongoing (oral) levodopa treatment schedule is 100 mg eight (8) times a day.

The administration of more than one dopamine precursor, agonist or combination thereof, in particular levodopa, carbidopa, apomorphine, and other drugs can be provided, either simultaneously or sequentially in time. Carbidopa or benserazide, for example, is often administered to ensure that peripheral carboxylase activity is completely shut down. Intramuscular, subcutaneous, oral and other administration routes can be employed. In one embodiment, these other agents are delivered to the pulmonary system. These compounds or compositions can be administered before, after or at the same time. In a preferred embodiment, particles that are administered to the respiratory tract include both Levodopa and carbidopa. The term "co-administration" is used herein to mean that the specific dopamine precursor, agonist or combination thereof and/or other compositions are administered at times to treat the episodes, as well as the underlying conditions described herein.

In one embodiment chronic levodopa therapy includes the use of the capsules of the invention in a dry powder inhaler for pulmonary delivery of levodopa combined with oral carbidopa. In another embodiment, pulmonary delivery of levodopa is provided during the episode, while chronic treatment can employ conventional oral administration of levodopa/carbidopa. In a further embodiment chronic levodopa therapy includes the use of the capsules of the invention in a dry powder inhaler for pulmonary delivery of levodopa combined with oral benserazide. In another embodiment, pulmonary delivery of levodopa is provided during the episode, while chronic treatment can employ conventional oral administration of levodopa/benserazide.

The present invention will be further understood by reference to the following non-limiting examples.

EXAMPLES

Example 1

This example summarizes a series of studies examining modifications performed on the spray drying operation for the production of a 90:8:2 levodopa:dipalmitoylphosphatidylcholine (DPPC):sodium chloride (NaCl) composition referred to herein as "90:8:2". The 90:8:2 spray drying operation that was developed for the production of initial lots of powders containing levodopa involved the production of a 90:8:2 levodopa:DPPC:NaCl powder that was fully amorphous with a water content of approximately 4%, a fine particle fraction in the range of 50-60%<5.4 microns and a maximum capsule fill weight of approximately 23 mg per size 00 capsule. This combination of properties resulted in a maximum delivered dose of levodopa (fine particle mass of levodopa) of approximately 12 mg per capsule, with these powders exhibiting a high degree of electrostatic charging and low bulk (typically 0.01-0.02 g/cc) and tap density (typically 0.02-0.04 g/cc), which made it extremely difficult to fill these powders reproducibly into size 00 capsules. Based on this, it was desired to attempt to increase the delivered dose of levodopa per capsule to 17 mg or greater. Additionally, it was desired to increase the physical stability of the 90:8:2 powder, as some powder lots were also observed to undergo an amorphous to crystalline conversion upon storage, particularly for lots that were filled under conditions for which the laboratory humidity was not controlled, thus potentially exposing these lots to elevated humidity.

During the spray drying operation, powder collected on the filter bags in the product filter is exposed to the moisture-laden environment of the product filter because of water vapor moving from the spray drying unit towards the exhaust across the product filter bags. When this powder is pulsed off the filter bags for collection, it tends to retain the residual moisture that it picked up in the product filter, which may act to facilitate a solid-state conversion from an amorphous to a crystalline form, either immediately or at some point during storage. To prevent this conversion, the powder must be dried effectively prior to collection, which is achieved by introducing dry nitrogen as a purge stream between the product filter and the collection vessel. However, during this drying operation, the powder becomes electrostatically charged, possibly due to bone dry conditions of the incoming nitrogen purge gas. This electrostatic charge decreases the bulk density of the powder, which in-turn decreases the amount of powder that can be filled in a capsule hence reducing the fine particle mass (FPM) per capsule. The methods and modifications indicated below were performed and evaluated for their ability to increase the FPM by eliminating the electrostatic charge on the powder and/or increasing the bulk density of the powder without predisposing the powder to solid-state conversion.

The studies described herein were thus conducted with the goals of (1) optimizing the fine particle mass (FPM) per capsule, (2) increasing the capsule fill weight and (3) stabilizing the amorphous solid state structure of bulk spray dried 90:8:2. Process parameter, unit operation and formulation modifications were executed and evaluated for their effectiveness in achieving endpoints (1-3).

Types of Modifications

Three types of modifications, (1) unit operation modifications, (2) process parameter modifications and (3) formulation modifications were evaluated.

(1) Unit Operation Modifications

Two types of unit operation modifications were studied, (i) the use of humidified purge gas and (ii) in-line ionization. Of these two, the use of humidified purge gas showed the best results with respect to decreasing electrostatic charge and increasing the maximum fill weight of the capsules. The details of this modification are described below.

Exposure to a humid environment helps decrease the static charge stored on a material because moisture in the air increases the conductivity of air, thereby enabling gas discharge. Since the dry nitrogen used as the purge gas to dry the powder was thought to be the primary cause for generation of the electrostatic charge on the 90:8:2 powder humidification of the purge gas may allow for charge dissipation and help eliminate the electrostatic charge stored on the surface of the powder particles. This can act to increase the bulk density, which will in-turn increase the fine particle mass per capsule.

Figure 2A:
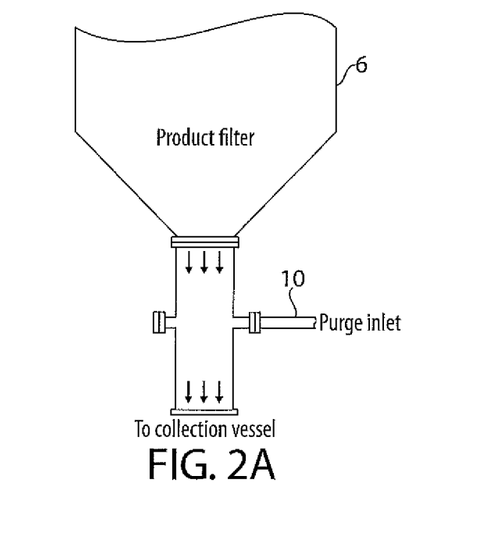
FIG. 2A is a schematic of a standard versus setup for introduction of purge gas.
Figure 2B:
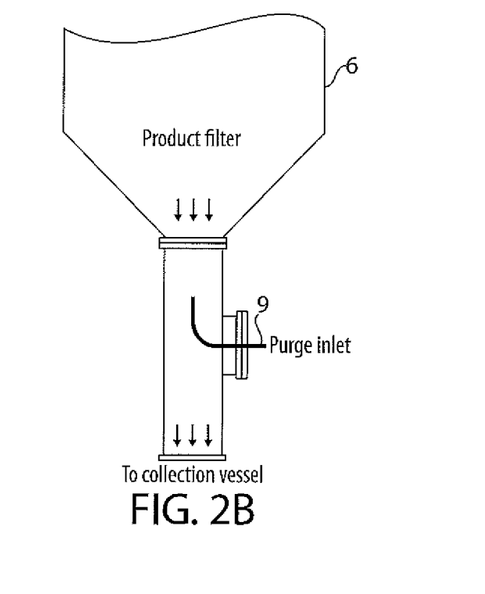
FIG. 2B is a schematic of an angled setup for introduction of purge gas.
Figure 3A:
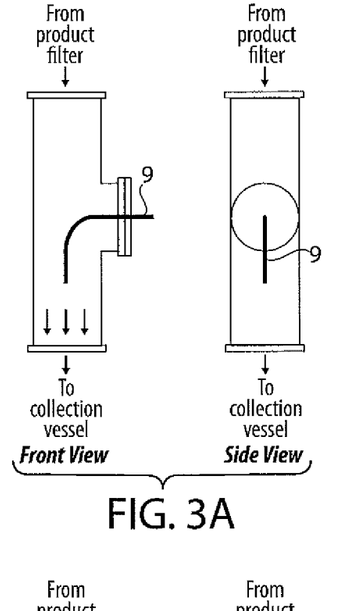
FIG. 3A is a schematic of an angled-inlet purge set up with a 0° downward facing purge stream.
Figure 3B:
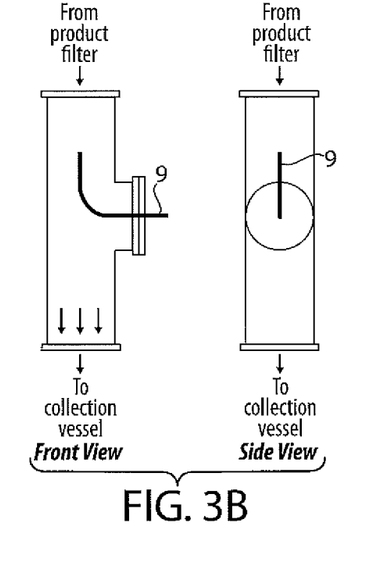
FIG. 3B is a schematic of an angled-inlet purge set up with a 0° upward facing purge stream.
Figure 3C:
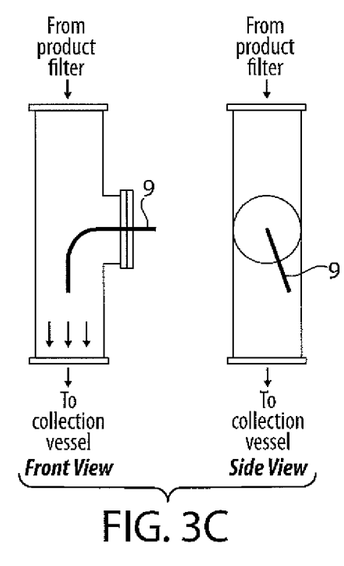
FIG. 3C is a schematic of an angled-inlet purge set up with a 25-30° downward facing purge stream.
Figure 3D:
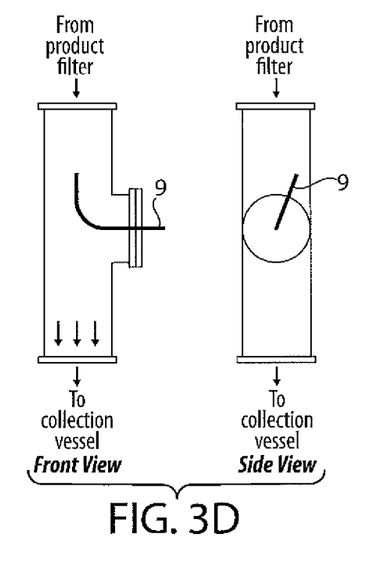
FIG. 3D is a schematic of an angled-inlet purge set up with a 25-30° upward facing purge stream.

Humidification of the purge gas was carried out using two types of purge inlet setups (i) a standard inlet setup as shown in FIG. 2A, in which the purge gas entered the product filter horizontally in at the bottom of the product filter and (ii) an angled inlet setup as shown in FIG. 2B, in which the purge gas enters the product filter at an angle to the vertical axis at the bottom of the product filter.

In a standard configuration, the powder pulsed off the product filter bags has contact with the dry purge gas for only a fraction of a second due to the narrow stream of purge gas entering in such a setup. By changing the angle of the purge gas inlet, as in the angled inlet configuration, one can increase the exposure time for powder pulsed off the bags to incoming dry purge gas. This setup may help more efficient elimination static charging as compared to a humidifying purge gas coming in through a standard horizontal inlet, which in turn may increase the fine particle mass and decrease the electrostatic charging of the powder.

Figure 1:
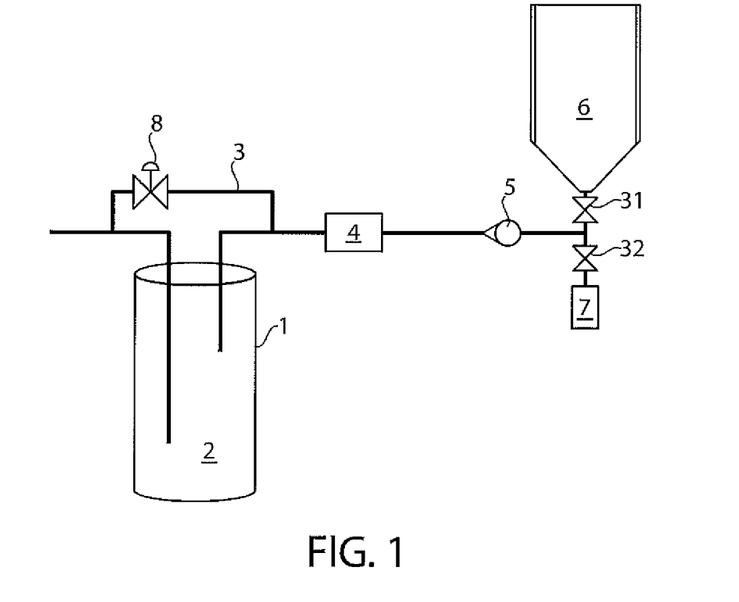
FIG. 1 is a schematic of a purge gas humidification setup using pressure pot.

Referring to FIG. 1A, humidification of the purge gas was carried out by passing the gas through a pressure pot 1 filled with water 2 for irrigation. A bypass line 3 with a control valve 8 was attached in parallel with the pressure pot 1. By controlling the ratio of the amount of nitrogen that passes through the pressure pot 1 to the amount that bypasses it, one can control the resulting relative humidity (RH) of the purge gas. Humidity of the exiting purge gas was measured using a dew-point meter 4 attached in series downstream of the humidification pressure pot 1 apparatus.

The purge gas is then passed through rotameter 5 which functions to control the flow of the purge gas to the product filter and facilitates adjusting the water content of the final powder. Butterfly valve 31 functions to isolate the product filter from the environment when the collection vessel 7 is changed. Butterfly valve 32 functions to isolate the collection vessel from the environment during the product transfer step from the collection vessel into a holding container which is stored at optimized temperature and relative humidity.

The humidified purge gas was then introduced at the bottom of the product filter apparatus 6 through (i) standard horizontal purge inlet (FIG. 2A), or (ii) angled purge inlet setup (FIG. 2B).

In an angled inlet setup (FIG. 2B), a directional inlet 9 for the purge gas stream was used, as opposed to a standard horizontal inlet 10 (FIG. 2A). This directional inlet 9 can be rotated along its own axis, and can hence be directed towards either the product filter 6 or the collection vessel 7 as shown in FIG. 1 and FIGS. 3A-D.

Directional inlet 9 configurations used included: downward 0° (FIG. 3A), upwards 0° (FIG. 3B), downwards angled 25-30° (FIG. 3C) and upwards angled 25-30° (FIG. 3D) with items in parenthesis indicating the angle to the vertical axis of the product filter.

Additionally, with the purge gas inlet at 0° to the vertical axis, different atomization gas flow (25 g/min to 55 g/min) rates were evaluated.

Experimental Conditions

Purge gas was humidified to different relative humidity levels. Rotameter for purge gas inlet was set to 3.5 g/min or 20 scfh.

Results

Standard Setup

Powders generated using nitrogen purge gas humidified to different RHs were observed to have similar particle sizes and fine particle fractions as compared to the powders manufactured under standard purge gas condition of 0% relative humidity (Table 1).

TABLE 1

FPF and geometric particle size distribution (gPSD) results for powders produced using different purge relative humidities.

| Purge gas humidification (% RH) | Fine particle fraction (%) | gPSD (μm) |
| --- | --- | --- |
| 10% RH (02098-1) | 57% | 7.6 |
| 20% RH (02096-0) | 54% | 5.3 |
| 40% RH (02098-2) | 52% | 7.8 |

However, visual observation of the powders indicated that the powders were much denser compared to the standard powder. Additionally, X-ray powder diffraction (XRPD) analysis of these powders showed evidence of crystalline peaks starting to form for the powders produced with purge gas humidities in excess of 10%. It is expected that this initial amount of crystalline phase will act to catalyze further recrystallization of these powders upon storage, which has been observed to result in undesirable decreases in FPF and water content. Thus, it was determined that a purge gas humidification in the range of 5-10% RH was optimal with respect to decreasing the electrostatic charge of the spray-dried powders utilizing the standard setup.

Angled Setup

The results obtained from the use of different orientations of the purge gas inlet and constant atomization gas flow rates are summarized in Table 2 below.

TABLE 2

FPF for different purge gas inlet orientations with constant atomization gas flow rate (22 g/min).

| Purge gas orientation (and angle to the vertical axis) | Purge gas relative humidity (%) | FPF (%) | Water content (%) |
|---|---|---|---|
| Downwards (0°) | 20 | Too much static charge | |
| Upwards (0°) | 15 | 54 | 3.35 |
| Downwards angled (25-30°) #1 | 10 | 34 | 3.32 |
| Downwards angled (25-30°) #2 | 10 | 53 | 3.52 |
| Upwards angled (25-30°) #1 | 10 | 53 | 3.91 |
| Upwards angled (25-30°) #2 | 10 | 53 | 3.89 |

The powder produced with a downward angled orientation could not be sampled due to the very high electrostatic charge present when the collection vessel was opened for sampling.

The results obtained from the use a single orientation of the purge gas inlet and a different atomization gas flow rates are summarized in Table 3 below.

TABLE 3

| FPF for upward facing purge gas inlet orientation with different atomization gas flow rates. | | | |
|---|---|---|---|
| Purge gas orientation (Angle to the vertical axis and RH) | Atomization gas flow rate (g/min) | FPF (%) | Water content (%) |
| Upwards (0° at 10% RH) | 25 | 49 | 4.01 |
| Upwards (0° at 10% RH) | 35 | 55 | 3.88 |
| Upwards (0° at 10% RH) | 45 | 56 | 3.95 |
| Upwards (0° at 10% RH) | 55 | 48 | 3.85 |
| Upwards (0° at 10% RH) | 30 | 55 | 2.64 |

Visually, all powders except for the one produced with downward angled orientation appeared to be much denser and to possess a relatively less amount of electrostatic charge as compared to the powders produced with the standard purge gas inlet orientation.

Results

Although humidification of the purge gas was observed to make the powders denser while keeping the FPF and water content the same, these formulations were observed in some cases to display evidence of the formation of a crystalline phase via XRPD, in particular for purge gas humidities in excess of 10%. As a result, the use of purge gas humidified to greater than 10% RH was determined to not be a viable option, with the use of a purge gas relative humidity in the range of 5 to 10% providing a mechanism for reducing powder electrostatic charge and increasing powder density without decreasing powder FPF or causing an amorphous to crystalline conversion.

(2) Formulation Modifications

Alternative formulations to the 90:8:2 levodopa:DPPC:NaCl powder were evaluated for their effectiveness in optimizing the FPF, fill weight and solid state stability.

Modification of DPPC:Sodium Chloride Ratio

Powders having an alternate ratio of DPPC:NaCl were evaluated for their efficiency in increasing the density and reducing electrostatic charging of the 90% levodopa powders. It was hypothesized that increasing the salt content of the powders could potentially act to help dissipate and thus reduce their electrostatic charge.

Experimental Design:

A DPPC:NaCl ratio of 4:6 was initially selected as a starting point to evaluate the influence of a higher amount of sodium chloride on the FPF and density of the 90:8:2 powders. Purge gas relative humidities were maintained at both 0% and 10%.

Results:

The physical and aerodynamic properties of 90:4:6 levodopa:DPPC:NaCl lots produced utilizing the standard conditions for the 90:8:2 formulation are shown in Table 4.

TABLE 4

| Analytical results for initial trial runs of 90:4:6 levodopa:DPPC:NaCl. | | | | | |
|---|---|---|---|---|---|
| levodopa:DPPC:NaCl Ratio | Purge gas RH (%) | FPF (%) | gPSD (um) | Bulk density (g/cc) | Tap density (g/cc) |
| 90:8:2 | 0 | 52 | 7.97 | 0.023 | 0.042 |
| 90:4:6 | 0 | 63 | 6.87 | 0.037 | 0.069 |
| 90:4:6 | 10 | 50 | 6.49 | 0.04 | 0.075 |

As can be seen in Table 4, the 90:4:6 levodopa:DPPC:NaCl powders produced possessed bulk and tap densities substantially higher than those seen for 90:4:6 levodopa:DPPC:NaCl powders made using similar conditions (typically 0.02 g/cc for bulk density and 0.04 g/cc for tap density). Since this trial produced favorable bulk and tap density results along with favorable results for FPF and gPSD, a decision was made to evaluate additional alternative DPPC:NaCl ratios of 2:8 and 6:4 and compare the results to 4:6 and control (8:2) powders. Results for powders produced utilizing the standard conditions for the 90:8:2 formulations are shown in Table 5.

TABLE 5

| Analytical results for alternative DPPC:NaCl ratios compared to the control. | | | | |
|---|---|---|---|---|
| levodopa:DPPC:NaCl ratio | FPF (%) | gPSD (um) | Bulk density (g/cc) | Tap density (g/cc) |
| 90:8:2 | 52 | 7.97 | 0.023 | 0.042 |
| 6:4 | 40 | | | |
| 90:4:6 | 63 | 6.87 | 0.037 | 0.069 |

Since a DPPC:NaCl ratio of 4:6 was observed to produce both high FPF and high bulk/tap density, this formulation was replicated to check for reproducibility. Results for the repeat runs for the 90:4:6 levodopa:DPPC:NaCl formulation are shown in Table 6 below.

TABLE 6

| Reproducibility runs for 90:4:6 levodopa:DPPC:NaCl. | | | | |
|---|---|---|---|---|
| levodopa:DPPC:NaCl (Run #) | FPF (%) | gPSD (um) | Bulk density (g/cc) | Tap density (g/cc) |
| 90:4:6 (Run # 1) | 41 | 9.13 | 0.04 | 0.05 |
| 90:4:6 (Run # 2) | 44 | | 0.03 | 0.04 |
| 90:4:6 (Run # 3) | 45 | | 0.04 | 0.06 |
| 90:4:6 (Run # 4) | 46 | 6.9 | 0.058 | 0.087 |
| 90:4:6 (Run # 5) | 53 | 6.4 | 0.055 | 0.091 |

Levodopa:DPPC:NaCl Formulations.

Based on these results, a DPPC:NaCl ratio of 5:5 was also produced and analyzed. The fine particle fraction, bulk/tap densities and geometric particle size for three runs of this formulation are summarized in Table 7 below.

TABLE 7

Reproducibility results for 90:5:5 levodopa:DPPC:NaCl formulation.

| levodopa:DPPC:NaCl (Run#) | FPF (%) | gPSD (um) | Bulk density (g/cc) | Tap density (g/cc) |
|---|---|---|---|---|
| 90:5:5 (Run # 1) | 51 | 7.4 | 0.039 | 0.054 |
| 90:5:5 (Run # 2) | 53 | 7.6 | 0.044 | 0.062 |
| 90:5:5 (Run # 3) | 51 | 6.5 | 0.044 | 0.066 |

The 90:5:5 levodopa:DPPC:NaCl formulations show very desirable FPF values, which are in the same range of the standard 90:8:2 levodopa:DPPC:NaCl formulation, and at the same time show desirable bulk and tap density values that were substantially increased as compared to the 90:8:2 formulation and are in the range of previously evaluated 90:4:6 levodopa:DPPC:NaCl formulation.

Addition of L-Leucine, Sodium Citrate or Calcium Chloride

The addition of excipients or substitution of excipients was also investigated as a potential route towards optimizing the FPM and bulk density of 90:8:2 powders. The excipients 1-leucine, sodium citrate and calcium chloride, which were available in-house, were used and evaluated as additives or as substitutes to the excipients currently in the 90:8:2 levodopa:DPPC:NaCl formulation.

Experimental Setup

Sodium citrate was evaluated as a potential alternative to Sodium chloride, Calcium chloride was investigated as another potential salt additive to the current formulation and 1-leucine was evaluated as a potential alternative to DPPC. When Calcium chloride was used, the amount of levodopa was reduced from 90% to 50%. The solid concentration for the solutions to be spray dried was maintained at 1 g/L.

Observations:

The results observed when 1-leucine, sodium citrate and calcium chloride are used as an additive or as a substitute in the formulation are summarized in Table 8 below.

TABLE 8

Analytical results from excipient addition and substitution to 90:8:2 powder.

| Formulation | Capsule fill weight (mg) | FPF (%) | gPSD (um) | Tap density (g/cc) | Bulk density (g/cc) |
|---|---|---|---|---|---|
| 90:8:2 LDOPA:Leucine:NaCl | 27.1 | 32 | 7.86 | 0.029 | 0.042 |
| 90:8:2 LDOPA:DPPC:NaCitrate | 27.3 | | | | |
| 50:25:15:10 LDOPA:DPPC:NaCitrate:CaCl2 | | 33 | | | |
| 50:25:15:10 LDOPA:DPPC:NaCitrate:CaCl2 | | 65 | | | |
| 50:25:15:10 LDOPA:DPPC:NaCitrate:CaCl2 | | 66 | | | |

DISCUSSION

Although addition of 1-leucine increased the tap and bulk densities of the powder, the FPF was significantly lower than that of the standard 90:8:2 levodopa:DPPC:NaCl formulation.

Substitution of sodium chloride by sodium citrate in the same ratio produced a capsule fill weight of 27.3 mg. An XRPD analysis of the powder concluded that it maintained its amorphous state. However, no other tests could be performed, as the yield was significantly low.

Addition of sodium citrate and calcium chloride, in addition to increasing the load of DPPC and reducing the load of Levodopa (50:25:15:10 Levodopa:DPPC:NaCitrate:CaCl$_2$) was observed to increase the FPF of the powder to 65%. However, XRPD analysis of the powder concluded the presence crystal growth.

Example 2

Optimization of Capsule Filling Operations

The standard 90:8:2 formulation powder is a low density powder with a high electrostatic charge. Because of the high volume which the low density 90:8:2 powders occupies, the amount of powder which can be filled into a capsule without affecting its aerodynamic performance is greatly limited. When such a low density powder has a high electrostatic charge, a high degree of variability can be seen in the fill weights of capsules due to the constant interaction of the charged powder with the walls of the capsules and the filling equipment. Capsule filling operations for such a powder, which displays a low fill weight and high weight variability at the same time, presented a set of unique challenges, all of which necessitated filling equipment modifications which helped achieve the fill weight goals without affecting the physical and chemical properties of the powder.

This example summarizes the experiments and modifications carried out the optimize the powder filling operations conducted using the Harro Hofliger KFM III-C capsule filling machine for filling 90:8:2 powders into size 00 capsules.

Different KFM III-C variables and formulation compositions were evaluated under different vacuum configurations for their effectiveness in achieving an optimal and reproducible fill weight with different 90:8:2 formulations. Three vacuum configurations were used (i) no vacuum to the dosators, (ii) Use of pre-installed KFM vacuum to the dosators, and (iii) Use of external vacuum to the dosators. For the 90:8:2 active powders, an external vacuum assisted size 00 full-bore vacuum dosator was determined to be the optimal configuration in order to achieve accurate and reproducible fill weights on the KFM III-C capsule filling machine. The analysis of this set up is described below.

Filling with the Use of External Vacuum on Dosator

In this vacuum setup, a Gast vacuum pump (model #1023-101Q-G608X) was used as a vacuum for the dosators instead of the vacuum on-board the KFM machine.

Dosator configurations and formulation variables that were evaluated for capsule filling accuracy and reproducibility using the external vacuum included:

(i) Standard size 00 vacuum dosator with 90:4:6 levodopa:DPPC:NaCl, (ii) Standard size 00 vacuum dosator with 90:8:2 levodopa:DPPC:NaCl, (iii) Standard size 00 vacuum dosator with 90:5:5 levodopa:DPPC:NaCl, (iv) Full bore size 00 vacuum dosator with 90:8:2 levodopa:DPPC:NaCl, and (v) Full bore size 00 vacuum dosator, size 4 plunging dosator and size 5 plunging dosator with lactose monohydrate NF.

Standard Size 00 Vacuum Dosator with 90:4:6 Levodopa:DPPC:NaCl:

For this experiment, the standard size 00 dosator was used to fill powder obtained by spray drying a 90:4:6 levodopa:DPPC:NaCl formulation. The variables evaluated for fill weight accuracy in this experiment included—(i) leveling blade versus platform for the powder bed, and (ii) low versus high powder bed height. The results for this experiment are summarized in Table 9 below.

TABLE 9

Average fill weights per capsule filling modification for 90:4:6 using external vacuum.

| 90:4:6 levodopa:DPPC:NaCl | Use of blade | Use of platform | Low bed height | High bed height |
|---|---|---|---|---|
| Average fill weight (mg) | 13.45 | 22.10 | 15.96 | 15.18 |

Standard Size 00 Vacuum Dosator with 90:8:2 Levodopa:DPPC:NaCl:

In this experiment, a standard size 00 dosator was used to fill 90:8:2 levodopa:DPPC:NaCl formulation. The variables evaluated for fill weight accuracy included (i) low powder bed height, (ii) use of blade and a rake to break down powder in the powder bed, and (iii) high versus low dosator vacuum. The results for this experiment are summarized in Table 10.

TABLE 10

Average fill weights per capsule filling modification for 90:8:2 using external vacuum.

| 90:8:2 levodopa:DPPC:NaCl | Low powder bed height | Use of blade | High vacuum | Low vacuum |
|---|---|---|---|---|
| Average fill weight (mg) | 8.30 | 28.25 | 26.36 | 7.2 |

Standard Size 00 Vacuum Dosator with 90:5:5 Levodopa:DPPC:NaCl:

In this experiment, a standard size 00 dosator was used to fill 90:5:5 levodopa:DPPC:NaCl formulation. In this experiment, only one variable was evaluated for fill weight accuracy—low dosator vacuum versus a high dosator vacuum. The results for this experiment are summarized in Table 11 below.

TABLE 11

Average fill weights per dosator vacuum modification for 90:5:5 using external vacuum.

| 90:5:5 levodopa:DPPC:NaCl | Fill weights | |
|---|---|---|
| Sample # | High vacuum | Low vacuum |
| Average fill weights (mg) | 29.2 | 22.06 |

Full Bore Size 00 Vacuum Dosator with 90:8:2 and 90:5:5 Levodopa:DPPC:NaCl

Figure 4:
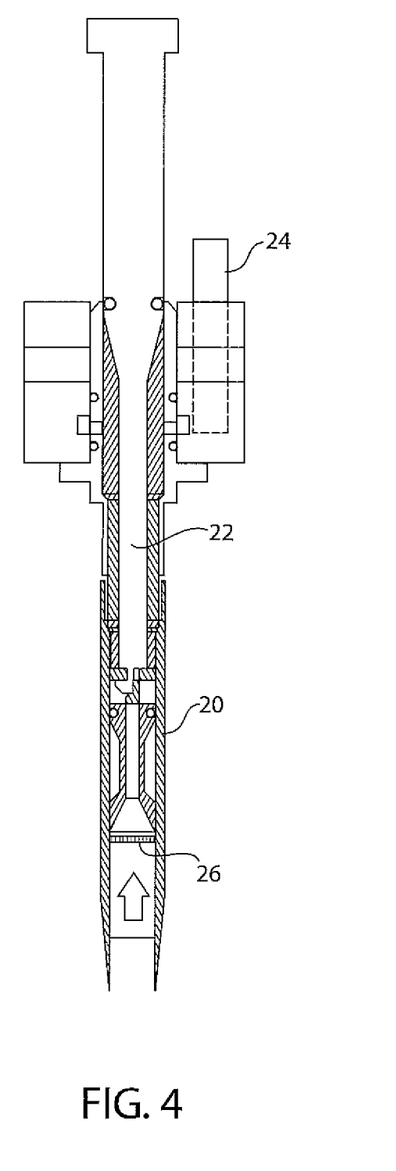
FIG. 4 is a schematic of the side view of a full bore dosator setup.
Figure 5:
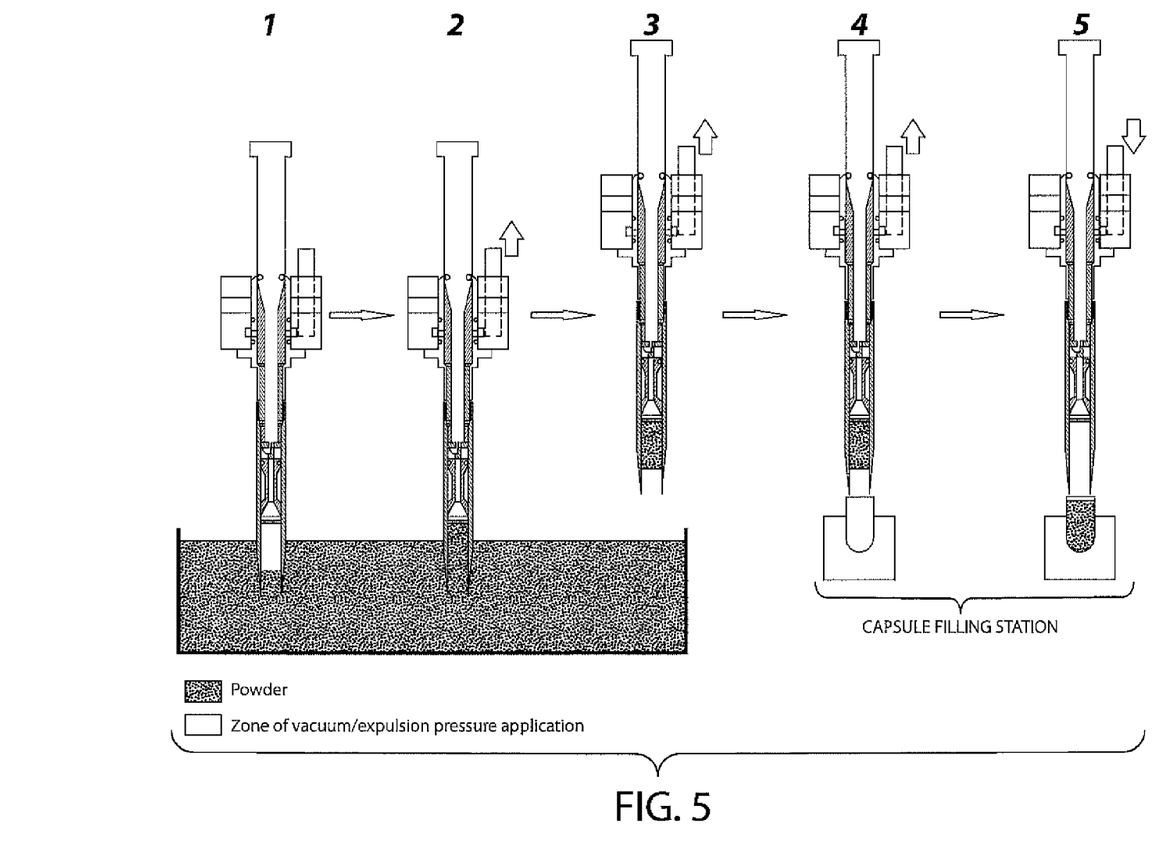
FIG. 5 is a schematic of the process steps in capsule filling operation utilizing the full bore dosator. The process is shown in five steps. Step 1 shows the dosator immersed into the powder bed. Step 2 shows the vacuum applied to the dosator that pulls the powder into the dosator. Step 3 shows the vacuum application continued, and the dosator moved from the powder bed to the capsule filling station. Step 4 shows the vacuum application continued and the dosator positioned above an empty capsule in the capsule filling station. Step 5 shoes the vacuum discontinued and expulsion pressure applied to the dosator expelling the powder from the dosator into the empty capsule thereby filling the capsule.

Referring now to FIG. 4, a full bore dosator 20 is a standard vacuum dosator which has been modified to increase the dosator chamber height. The dosator 20 was modified in such a way that the dosator plunger 22 stays stationary, and powder is pulled into the dosator 20 by applying a vacuum and expelled out of the dosator 20 by applying expulsion pressure as illustrated in the schematic of FIG. 5. Vacuum was generated by means of a pump attached to the dosator 20 at the port 24 with appropriate tubing. A two (2) micron mesh 26 was added at the bottom of the plunger 22 to prevent powder from crossing over and interfering with the vacuum pump and tubing. Expulsion pressure was provided by means of compressed nitrogen sourced from an external storage tank.

In this experiment, a full bore vacuum dosator was used for filling 90:8:2 powder which was produced using a nitrogen gas overlay on the aqueous phase. As discussed previously, the 90:5:5 90:8:2 powder formulations were observed to have almost twice the original fill weights due to increased bulk density and tap density values. Using a full-bore vacuum dosator, it was possible to produce similar high fill weights using the standard 90:8:2 90:8:2 powder.

To achieve the target capsule fill weight, the dosator chamber height was dialed in against a standard vacuum of −15" Hg, until capsules having sufficient accuracy and reproducibility of the desired fill weight were produced. The temperature of the room was maintained around 20° C. and the relative humidity of the room was maintained around 20% R.H.

One lot of 90:8:2 levodopa:DPPC:NaCl was filled for a trial fill, followed by another lot of the same composition. After these two lots were produced, a third lot with 90:5:5 levodopa:DPPC:NaCl was filled. All 3 lots are evaluated for the KFM's effectiveness in producing an accurate and reproducible fill weight.

The results for this experiment are summarized in Table 12 below.

TABLE 12

Target fill weights and average fill weights for 90:8:2 LDOPA:DPPC:NaCl formulation filled using a full bore vacuum dosator.

| levodopa:DPPC:NaCl | Target fill weight (mg) | Average fill weight (mg) | Relative standard deviation (%) |
|---|---|---|---|
| 90:08:02 | 35 | 34.49 | 3.40% |
| 90:08:02 | 38 | 38.26 | 3.50% |
| 90:05:05 | 38 | 36.03 | 13.60% |

Previous attempts at filling to 90:8:2 formulations resulted in a maximum fill weight of 23 milligrams per capsule. The fill weights obtained using the full bore vacuum dosator are significantly greater than the previous attempts. For example, fill weights of 28 to 40 mg may be achieved. Examples of fill weights include, but are not limited to, 28-32 mg, 30-34 mg, or 35-40 mg.

Full Bore Size 00 Vacuum Dosator, Size 4 Plunging Dosator and Size 5 Plunging Dosator with Lactose Monohydrate NF:

Lactose monohydrate NF was used as a placebo for the 90:8:2 formulation. The target fill weight of lactose was 10 mg.

CONCLUSION

Typical filling of large amounts of powder are uncommon for pulmonary products. Applicants have identified new parameters and processes which allow for filling large amounts of powder in a capsule for pulmonary delivery. For the 90:8:2 active powders, an external vacuum assisted size 00 full-bore vacuum dosator can be used in order to achieve higher maximum fill weights (up to 38 mg or higher) as compared to the previous maximum fill weight of 23 mg seen for the 90:8:2 powder, as well as accurate and reproducible fill weights on the KFM III-C capsule filling machine.

Additionally, of the three ratios of powders that were evaluated using this setup, the powder with an levodopa:DPPC:NaCl ratio of 90:8:2 can be filled much more accurately and reproducibly to the target fill weight, as compared to the 90:5:5 and 90:4:6 ratios.

For the Lactose placebo powder, an external vacuum assisted size 5 plunger dosator is the setup of choice to achieve the desired target weight accurately and reproducibly.

Example 3

Analysis of Capsule Materials and Emitted Dose

It was hypothesized that certain types of capsules may be useful in increasing the emitted dose of powder. HPMC "clear" capsules and HPMC/titanium dioxide "white" capsules were chosen. Two workstations with an inhaler configured with emitted dose tubes were provided. Clear or white capsules were filled to 28 mg with inhalable levodopa powder (dry weight ratio of 90:8:2 of levodopa:DPPC:NaCl) prepared in accordance with Example 1 to a target load and placed in the inhaler. An analyst was assigned to each station and actuated the inhaler into the ED tube at 28.3 L/min for 4.2 seconds and rinsed for content. The FPF of the content was measured using standard procedures. Analysts also switched work stations and used each other's inhaler technique. The results are provided in the following Tables 13-20. Tables 13 and 14 show the comparison of white capsule sourced from Shionogi, Inc. as compared to the clear capsule (no titanium dioxide). Tables 15 and 16 show the same study but the analysts have switched workstations and used each other's inhaler technique. Tables 17 and 18 are a compilation of the results from Tables 15 and 16. Tables 19 and 20 show the comparison of a white capsule sourced from Capsugel as compared to the clear capsule (no titanium dioxide).

TABLE 13

| FPF$_{TD}$ <5.6% (N = 10 Per Analyst Per Capsule Type) | | | |
|---|---|---|---|
| FPF | Analyst 1 | Analyst 2 | Average |
| White Capsule | 53 | 49 | 51 |
| Clear Capsule | 46 | 42 | 44 |

TABLE 14

| FPF$_{ED}$ <5.6% (N = 10 per Analyst Per Capsule Type) | | | |
|---|---|---|---|
| FPF | Analyst 1 | Analyst 2 | Average |
| White Capsule | 54 | 49 | 52 |
| Clear Capsule | 49 | 45 | 47 |

TABLE 15

| FPF$_{TD}$ <5.6% (N = 5 Per Analyst Per Capsule Type) | | | |
|---|---|---|---|
| FPF | Analyst 1 | Analyst 2 | Average |
| White Capsule | 49 | 51 | 50 |
| Clear Capsule | 44 | 40 | 42 |

TABLE 16

| FPF$_{ED}$ <5.6% (N = 5 Per Analyst Per Capsule Type) | | | |
|---|---|---|---|
| FPF | Analyst 1 | Analyst 2 | Average |
| White Capsule | 50 | 52 | 51 |
| Clear Capsule | 47 | 45 | 46 |

TABLE 17

| FPF$_{TD}$ <5.6% (N = 15 per Analyst Per Capsule Type) | | | |
|---|---|---|---|
| FPF | Analyst 1 | Analyst 2 | Average |
| White Capsule | 52 | 49 | 51 |
| Clear Capsule | 45 | 42 | 44 |

TABLE 18

| FPF$_{ED}$ <5.6% (N = 15 per Analyst Per Capsule Type) | | | |
|---|---|---|---|
| FPF | Analyst 1 | Analyst 2 | Average |
| White Capsule | 53 | 50 | 52 |
| Clear Capsule | 48 | 45 | 47 |

TABLE 19

| FPF total dose <5.6% | | | |
|---|---|---|---|
| FPF | Analyst 1 | Analyst 2 | Average |
| White Capsule (n = 10) | 47 | 42 | 45 |
| Clear Capsule (n = 2) | 46 | 39 | 43 |

TABLE 20

| FPF emitted dose <5.6% | | | |
|---|---|---|---|
| FPF | Analyst 1 | Analyst 2 | Average |
| White Capsule (n = 10) | 52 | 46 | 49 |
| Clear Capsule (n = 2) | 51 | 43 | 47 |

DISCUSSION

The data shows that more powder was emitted from the white capsules having a capsule material that comprises HPMC and titanium dioxide as compared to the powder emitted from the clear capsules that do not contain titanium dioxide in the capsule material. This data is surprising. Without being limited to any theory, it is believed that the titanium dioxide present in the capsule material reduces the amount of powder that sticks to the capsule wall upon emptying from the capsule.

Example 4

Stability Studies

Purpose

To characterize 90/8/2 and 90/5/5 Levodopa powder in machine filled capsules that have been exposed to 75% relative humidity and 25° C. conditions for 15, 30 and 60 minutes using gravimetric ACI-3 and XRPD. Additional time points were added at 240 and 360 minutes of exposure, white and clear capsules were tested with lot 41021 (90/8/2).

Experimental Design:

Samples from Lot 28100 (90/8/2) and Lot 28109 (90/5/5) were exposed to pre-stated conditions in a humidity chamber and then immediately analyzed.

TABLE 21

Data Summary (clear capsules):

| | Lot | | | | | |
|---|---|---|---|---|---|---|
| | 28100 | | | 28109 | | |
| Time Exposed (minutes) | 15 | 30 | 60 | 15 | 30 | 60 |
| Average FPF <5.6 μm Relative to Change in Capsule Weight (%) | 57 | 62 | 58 | 51 | 52 | 52 |
| XRPD Results | A | A | A | A | A | A |

A = Amorphous
C = Crystalline

TABLE 22

Data Summary (white vs. clear capsules):

| | Lot | | | |
|---|---|---|---|---|
| | 41021 White Capsule | | 41021 Clear Capsule | |
| Time Exposed (minutes) | 240 | 360 | 240 | 360 |
| Average FPF <5.6 μm Relative to Change in Capsule Weight (%) | 24 | 20 | 23 | 22 |
| XRPD Results | C | C | C | C |

A = Amorphous
C = Crystalline

Materials and Methods
1. Material
Hand Filled 90% L-Dopa Capsules Blistered in white and clear HPMC capsules
4 capsules per pull
Filled with Lot 41018
2. Test Schedule
Capsules will be stored in 25° C./75% RH chamber for the times listed below in Table 23. Capsules will be tested with the capsule cap on during exposure and the cap off during exposure for each type of capsule.

TABLE 23

| Condition | Time Point | 30 Min | 60 Min | 120 Min | 240 Min |
|---|---|---|---|---|---|
| 25° C./ 75% RH | FPF, grav (n = 1) | X | X | X | X |
| | gPSD (n = 1) | X | X | X | X |
| | XRPD (n = 1) | X | X | X | X |

3. Results
a. gPSD

TABLE 24

| | gPSD | | | |
|---|---|---|---|---|
| | Capsule | | | |
| Time Point | White Cap | White No Cap | Clear Cap | Clear No Cap |
| 30 Min | 8.4 | 8.2 | 8.0 | 8.5 |
| 60 Min | 8.2 | 8.5 | 8.6 | 8.8 |
| 120 Min | 9.5 | 8.7 | 8.7 | 8.8 |
| 240 Min | 8.7 | 8.7 | 9.0 | 8.3 | b. XRPD

TABLE 25

| | XRPD | | | |
|---|---|---|---|---|
| | Capsule | | | |
| Time Point | White Cap | White No Cap | Clear Cap | Clear No Cap |
| 30 Min | Amorphous | Amorphous | Amorphous | Amorphous |
| 60 Min | Amorphous | Amorphous | Amorphous | Amorphous |
| 120 Min | Amorphous | Amorphous | Amorphous | Amorphous |
| 240 Min | Amorphous | Amorphous | Amorphous | Amorphous | c. % FPF<5.6 μm

TABLE 26

| | % FPF <5.6 μm | | | |
|---|---|---|---|---|
| | Capsule | | | |
| Time Point | White Cap | White No Cap | Clear Cap | Clear No Cap |
| 30 Min | 57% | 53% | 56% | 61% |
| 60 Min | 65% | 58% | 56% | 56% |
| 120 Min | 61% | 64% | 59% | 59% |
| 240 Min | 64% | 61% | 57% | 58% |

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims. It should also be understood that the embodiments described herein are not mutually exclusive and that features from the various embodiments may be combined in whole or in part in accordance with the invention.

What is claimed:

1. A capsule for use in an inhalation device, wherein the capsule is filled with a dry powder comprising levodopa; wherein the capsule's shell comprises hydroxypropyl methylcellulose and titanium dioxide, and wherein the dry powder comprises a fine particle fraction of at least 50% of the nominal powder dose.

2. The capsule of claim 1, wherein the dry powder comprises from about 2% to about 8% of water by weight.

3. The capsule of claim 2, wherein the dry powder comprises from about 5% to about 6% of water by weight.

4. The capsule of claim 1, wherein the capsule is a 00 size capsule.

5. The capsule of claim 4, wherein the dry powder comprises between about 15 milligrams and 50 milligrams of levodopa.

6. The capsule of claim 5, wherein the dry powder comprises between about 25 milligrams and 35 milligrams of levodopa.

7. The capsule of claim 1, wherein the dry powder further comprises a salt.

8. The capsule of claim 7, wherein said salt is sodium chloride.

9. The capsule of claim 1, wherein the dry powder further comprises a phospholipid.

10. The capsule of claim 9, wherein said phospholipid is dipalmitoylphosphatidylcholine (DPPC).

11. The capsule of claim 1, wherein the dry powder further comprises DPPC and sodium chloride.

12. The capsule of claim 1, wherein the dry powder comprises a fine particle fraction between about 50% to about 70% of the total amount of powder in the capsule.

13. The capsule of claim 1, wherein the capsule is filled with about 30 milligrams to about 50 milligrams of dry powder.

14. The capsule of claim 1, wherein the dry powder has a working density between about 0.02 $g/cm^3$ to about 0.1 $g/cm^3$.

15. The capsule of claim of claim 1, wherein the dry powder has a working density between about 0.02 $g/cm^3$ to about 0.05 $g/cm^3$.

\* \* \* \* \*